United States Patent
Goetzl et al.

(10) Patent No.: US 10,962,555 B2
(45) Date of Patent: Mar. 30, 2021

(54) PURIFICATION, EXTRACTION AND ANALYSES OF FETAL NEURALLY-DERIVED EXOSOMES IN MATERNAL BLOOD AND NEONATAL NEURALLY-DERIVED EXOSOMES FROM NEONATAL BLOOD

(71) Applicant: Temple University—Of The Commonwealth System of Higher Education, Philadelphia, PA (US)

(72) Inventors: Laura Goetzl, Philadelphia, PA (US); Edward Goetzl, San Francisco, CA (US)

(73) Assignee: TEMPLE UNIVERSITY-OF THE COMMONWEALTH SYSTEM OF HIGHER EDUCATION, Philadelphia, PA (US)

(*) Notice: Subject to any disclaimer, the term of this patent is extended or adjusted under 35 U.S.C. 154(b) by 210 days.

(21) Appl. No.: 16/068,738

(22) PCT Filed: Jan. 6, 2017

(86) PCT No.: PCT/US2017/012478
§ 371 (c)(1),
(2) Date: Jul. 9, 2018

(87) PCT Pub. No.: WO2017/120436
PCT Pub. Date: Jul. 13, 2017

(65) Prior Publication Data
US 2019/0025329 A1 Jan. 24, 2019

Related U.S. Application Data

(60) Provisional application No. 62/275,964, filed on Jan. 7, 2016.

(51) Int. Cl.
*G01N 33/68* (2006.01)
*C12Q 1/6883* (2018.01)

(52) U.S. Cl.
CPC ....... *G01N 33/6896* (2013.01); *C12Q 1/6883* (2013.01); *G01N 2800/385* (2013.01)

(58) Field of Classification Search
CPC ......... G01N 33/6896; G01N 2800/385; C12Q 1/6883
See application file for complete search history.

(56) References Cited

U.S. PATENT DOCUMENTS 8,568,994 B2 * 10/2013 Altevogt ............. G01N 33/689
435/7.21

FOREIGN PATENT DOCUMENTS

GB 2463401 3/2010

OTHER PUBLICATIONS

Bianchi et al. "DNA sequencing versus standard prenatal aneuploidy screening." N Engl J Med. 2014;370(9):799-808.
Derfuss et al., "Contactin-2/TAG-1-directed autoimmunity is identified in multiple sclerosis patients and mediates gray matter pathology in animals", Proc Natl Acad Sci U S A, (20090519), vol. 106, No. 20, pp. 8302-8307, XP055396932.
Fan et al. "Non-invasive prenatal measurement of the fetal genome." Nature. 2012;487(7407):320-324.
Fiandaca et al. "Identification of preclinical Alzheimer's disease by a profile of pathogenic proteins in neurally derived blood exosomes: A case-control study." Alzheimers Dement. 2015;11(6):600-7.e1.
Goetzl et al. "Altered lysosomal proteins in neural-derived plasma exosomes in preclinical Alzheimer disease." Neurology. 2015;85(1):40-47.
Goetzl et al. "Low neural exosomal levels of cellular survival factors in Alzheimer's disease." Ann Clin Transl Neurol. 2015;2(7):769-773.
Hsiao et al., "Effects of early postnatal ethanol intubation on GABAergic synaptic proteins", Brain Res Dev Brain Res, (20021020), vol. 138, No. 2, pp. 177-185, XP055396929.
Kapogiannis et al. "Dysfunctionally phosphorylated type 1 insulin receptor substrate in neural-derived blood exosomes of preclinical Alzheimer's disease." FASEB J. 2015;29(2):589-596.
Kitzman et al. "Noninvasive whole-genome sequencing of a human fetus." Sci Transl Med. 2012;4(137):137ra76.
Lo et al. "Quantitative analysis of fetal DNA in maternal plasma and serum: implications for noninvasive prenatal diagnosis." Am J Hum Genet. 1998;62(4):768-775.
Norton et al. "Cell-free DNA analysis for noninvasive examination of trisomy." N Engl J Med. 2015;372(17):1589-1597.

* cited by examiner

*Primary Examiner* — Olga N Chernyshev
(74) *Attorney, Agent, or Firm* — Riverside Law LLP

(57) ABSTRACT

The present invention provides for the first time the identification of fetal neural exosomal biomarkers isolated from maternal plasma useful in diagnosing fetal neurodevelopmental outcomes. The invention also provides the identification of neonatal neural exosomal biomarkers isolated from neonatal plasma useful in diagnosing neonatal neurodevelopmental outcomes The present invention therefore provides methods, kits and systems for diagnosing fetal neurodevelopmental outcomes, by examining relevant proteins and RNA in fetal neural exosomes isolated from a maternal plasma and neonatal neural exosomes isolated from neonatal plasma.

5 Claims, 6 Drawing Sheets

Neural markers

| Fetal neural exosomes | n | CD81 | NS-enolase | NF light chain | L1CAM |
|---|---|---|---|---|---|
| Heavy EtOH Exposure | 10 | 1075±66.3 | 1942±372 | 1087±108 | 353±19.2 |
| Healthy pregnancy | 10 | 984±77.8 | 2600±290 | 989±81.9 | 340±34.8 |
| Non-pregnant controls | 16 | 33.3±1.87 | <100 | <20 | <10 |
| Total neural exosomes | | | | | |
| Non-pregnant controls | 16 | 4257±135 | 2823±239 | 750±104 | — |

Fetal and placental markers

| Fetal neural exosomes | n | CD81 | Sonic Hedgehog | PSG-1 (ng/ml) |
|---|---|---|---|---|
| Heavy EtOH Exposure | 10 | 1075±66.3 | 409±59.6 | <3 |
| Healthy pregnancy | 20 | 784±63.1 | 646±104 | 5.35±1.14 |
| Non-pregnant controls | 16 | 33.3±1.87 | 63.3±14.6 | <3 |
| Placental extracts | 6 | 27.4±7.47 | — | 314±55.6 |

Figure 1

| Fetal neural exosomes | n | Synaptophysin | GAP-43 | Synaptotagmin | Synaptopodin |
|---|---|---|---|---|---|
| Heavy EtOH Exposure | 10 | 379±26 | 163±84 | 60392±24153 | 397±86 |
| Healthy pregnancy | 10 | 1791±732 | 406±108 | 264065±454405 | 706±138 |
| Non-pregnant controls | 16 | 28±6 | 96±96 | 4823±3841 | 18±4 |

*All Values Normalized to CD81

Figure 3

PURIFICATION, EXTRACTION AND ANALYSES OF FETAL NEURALLY-DERIVED EXOSOMES IN MATERNAL BLOOD AND NEONATAL NEURALLY-DERIVED EXOSOMES FROM NEONATAL BLOOD

CROSS-REFERENCE TO RELATED APPLICATIONS

This application is a U.S. national phase application filed under 35 U.S.C. § 371 claiming benefit to PCT International Patent Application No. PCT/US2017/012478, filed on Jan. 6, 2017, which is entitled to priority to U.S. Provisional Application No. 62/275,964, filed Jan. 7, 2016, each of which is incorporated by reference herein in its entirety.

BACKGROUND OF THE INVENTION

The prevalence of autism, attention deficit hyperactivity disorder (ADHD) and other neurodevelopmental conditions with potential in utero etiologies have been increasing over time (Boyle et al., 2011, Pediatrics 127:1034-42). In utero exposure to chemicals, medications, infections/excess inflammation, unfavorable nutritional conditions, or innate neurodevelopmental conditions, can disrupt fetal brain development, deplete subpopulations of neurons and adversely affect the formation of normal synaptic connections (Rees et al., 2005, Early Hum Dev 81:753-61; Zimmerman and Conners (eds), 2010, Clinical and Research Aspects 978-1-60327-920-8). A major roadblock to unraveling the mechanisms and timing of neurodevelopmental derangement is the almost complete absence of sensitive non-invasive assessments. Recent advances in prenatal diagnosis demonstrate that fetal DNA can both cross the placenta and be isolated from first trimester maternal blood (Lo et al., 1998, Am J Hum Genet 62, 768-75; Fan et al., 2012, Nature 487:320-4; Kitzman et al., 2012, Sci Transl Med 4:137ra76; Bianchi et al., 2015, NJEM 370:799-808; Norton et al., 2014, NJEM 372:1589-97). In adult populations, neural exosomes cross the mature blood brain barrier (BBB) and can be isolated for detection of pre-clinical Alzheimer's disease (Kapogiannis et al., 2015, Faseb J 29:589-96; Fiandaca et al., 2015, Alzheimers Dement 11:600-7; Goetzl et al., 2015, Neurology 85:40-7; Goetzl et al., 2015, Ann Clin Trans Neurol 2:769-73).

Thus, there is an urgent need in the art for compositions and methods for non-invasive diagnosis of neurodevelopmental conditions in utero. The present invention addresses these needs.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts the fetal neural exosome protein markers. Each value is mean pg/ml±SEM, except for PSG-1, which is in ng/ml. Differences in CD81 and Sonic Hedgehog between pregnancies with heavy ethanol (EtOH) exposure or healthy pregnancies and non-pregnant controls are significant at $p<0.0001$, as determined by an unpaired t test. Differences in PSG-1 between FAS or healthy pregnancies or non-pregnant controls and placental extracts are significant at $p<0.0001$, as determined by an unpaired t test.

FIG. 3 depicts experimental results demonstrating low neuronal exosomal levels of synaptogenically-critical proteins in fetal alcohol syndrome compared to healthy pregnancies. The means values are presented. The significance of differences between levels of Synaptophysin ($p<0.001$), GAP-43 ($p<0.0001$), Synaptotagmin ($p<0.0001$), Synaptopodin ($p<0.0001$) for the HP and FAS pregnancy groups was calculated by an unpaired t test.

SUMMARY OF THE INVENTION

Figure 2:
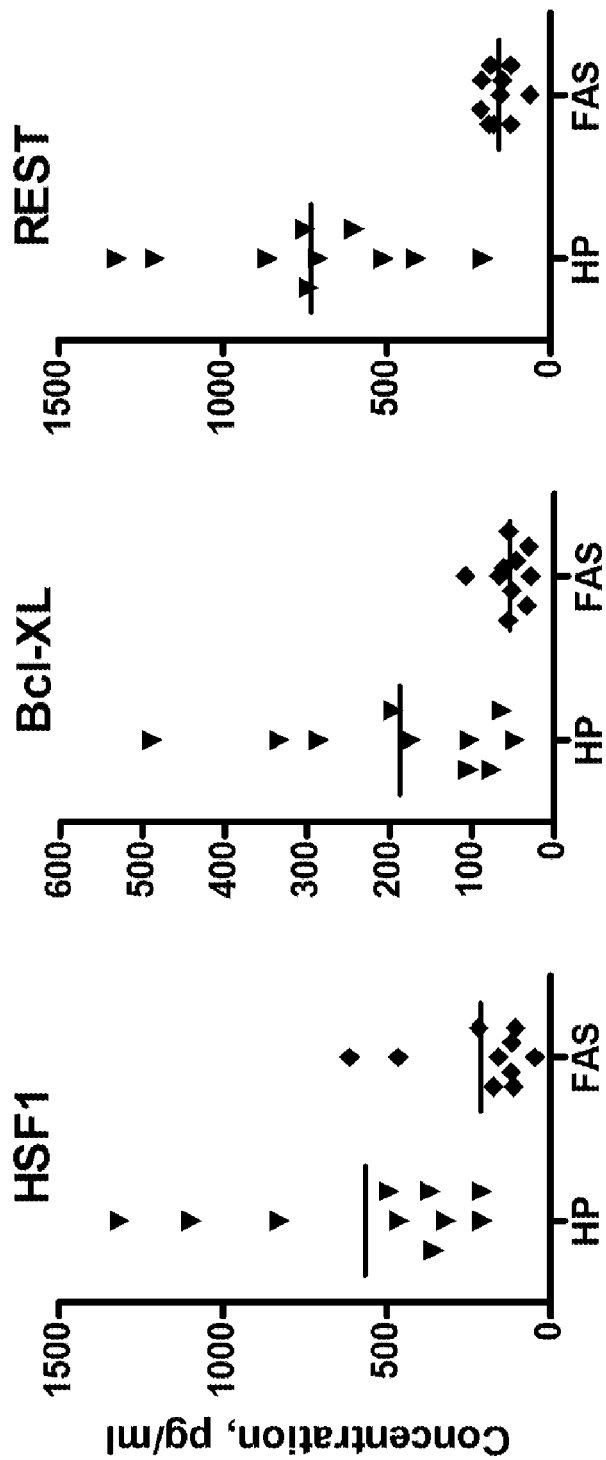
FIG. 2 depicts experimental results demonstrating decreased fetal neural exosome levels of neuronal survival factors in FAS. Each point represent a value for a control healthy pregnancy (HP, n=10) or pregnancy with heavy alcohol exposure (FAS, n=10) and each horizontal line depicts the mean for that group of values. The significance of differences between levels of HSF1 ($p=0.0267$), Bcl-XL ($p=0.0092$) and REST ($p<0.0001$) for the HP and FAS pregnancy groups was calculated by an unpaired t test.

In one aspect, the present invention provides a method of diagnosing neurodevelopmental disorder in a subject. In one embodiment, the method comprises providing a biological sample, isolating an vesicle from the biological sample, determining the level of a biomarker in the vesicle, comparing the level of the biomarker in the biological sample with a comparator control, and diagnosing the subject with the neurodevelopmental disorder when the level of the biomarker in the biological sample is altered at a statistically significant amount when compared with the level of the biomarker of the comparator control.

In one embodiment, the neurodevelopmental disorder is a fetal neurodevelopmental disorder or a neonatal neurodevelopmental disorder.

In one embodiment, the subject is a neonatal subject or an in utero fetal subject.

In one embodiment, biological sample is a sample from a gestational carrier of the fetal subject, or a sample from the neonatal subject. In one embodiment, biological sample is provided during a first trimester of gestation.

In one embodiment, the vesicle is selected from the group consisting of exosomes, microparticles, microvesicles, nanosomes, extracellular vesicles, and ectosomes. In one embodiment, the vesicle is a fetal neural exosome (FNE) or neonatal neural exosome.

In one embodiment, the biomarker is selected from the group consisting of CD81, Sonic Hedgehog, type 1 pregnancy specific β-1-glycoprotein (PSG-1), heat shock factor 1 (HSF1), B-cell lymphoma-extra large mitochondrial membrane protein (Bcl-XL), restriction element-1 silencing transcription factor (REST), Synaptophysin, Synaptotagmin, Synaptopodin, GAP-43, neurogranin, morphine receptor (MU), and any combination thereof.

In one embodiment, fetal neurodevelopmental disorder is selected from the group consisting of fetal alcohol syndrome, autism, attention deficit hyperactivity disorder (ADHD) hypoxic ischemic encephalopathy, congenital cytomegalovirus (CMV) infection, zika virus infection, neonatal abstinence syndrome (NAS), and cerebral palsy.

In one embodiment, the comparator control is the level of the biomarker in the biological sample of a healthy subject. In one embodiment, the level of the biomarker in the biological sample of subject is increased at a statistically significant amount when compared with the level of the biomarker of the comparator control. In one embodiment, the level of the biomarker in the biological sample of subject is decreased at a statistically significant amount when compared with the level of the biomarker of the comparator control. In one embodiment, the comparator control is at least one selected from the group consisting of: a positive control, a negative control, a historical control, a historical norm, or the level of a reference molecule in the biological sample.

In one embodiment, the level of the biomarker in the biological sample is determined by measuring the level of mRNA of the biomarker in the biological sample. In one embodiment, the level of the biomarker in the biological sample is determined by measuring the level of polypeptide of the biomarker in the biological sample.

In another aspect, the invention provides a method for diagnosing fetal alcohol syndrome (FAS) in a fetal subject. In one embodiment, the method comprises providing a biological sample from a gestational carrier of the fetal subject, isolating a fetal neural exosome from the biological sample, determining the level of a biomarker in the exosome, comparing the level of the biomarker in the biological sample with a comparator control, and diagnosing the fetal subject with FAS when the level of the biomarker in the biological sample is altered at a statistically significant amount when compared with the level of the biomarker of the comparator control.

In one embodiment, the biomarker is selected from HSF1, Bcl-XL, REST, Synaptophysin, Synaptotagmin, Synaptopodin, GAP-43, and any combination thereof.

In one embodiment, fetal subject is diagnosed with FAS when the level of the biomarker in the biological sample is lower than the level of the biomarker of the comparator control.

In one aspect, the invention provides a method for isolating a fetal exosome from a biological sample. In one embodiment, the method comprises obtaining a biological sample from a pregnant subject; isolating a total exosome population from the biological sample; contacting the total exosome population with an agent, wherein the agent comprises a moiety that binds the fetal exosome and a label; contacting the agent with a substrate comprising a moiety that binds the label to form a complex consisting of the substrate, the agent and the fetal exosome; and isolating the complex.

In one embodiment, the fetal exosome is a fetal neural exosome.

In one embodiment, the biological sample is plasma.

In one embodiment, the agent is an antibody. In one embodiment, the antibody is a Contactin-2/TAG1 antibody.

In one embodiment, the label is biotin and the substrate comprises streptavidin.

In one embodiment, the subject is human.

In another aspect, the invention provides a kit for diagnosing a fetal neurodevelopmental disorder in an in utero fetal subject. In one embodiment, the kit comprises a reagent for isolating a vesicle from a biological sample and a reagent for measuring the level of a biomarker in the vesicle.

In one embodiment, the vesicle is selected from the group consisting of exosomes, microparticles, microvesicles, nanosomes, extracellular vesicles, and ectosomes. In one embodiment, the vesicle is a fetal neural exosome.

In one embodiment, the biomarker is selected from the group consisting of CD81, Sonic Hedgehog, type 1 pregnancy specific β-1-glycoprotein (PSG-1), heat shock factor 1 (HSF1), B-cell lymphoma-extra large mitochondrial membrane protein (Bcl-XL), restriction element-1 silencing transcription factor (REST), Synaptophysin, Synaptotagmin, Synaptopodin, GAP-43, neurogranin, morphine receptor (MU), and any combination thereof.

In one embodiment, the fetal neurodevelopmental disorder is selected from the group consisting of autism, attention deficit hyperactivity disorder (ADHD), hypoxic ischemic encephalopathy, congenital cytomegalovirus (CMV) infection, zika virus infection, neonatal abstinence syndrome (NAS), and cerebral palsy.

In one embodiment, the biological sample is plasma obtained from a gestational carrier of the in utero fetal subject. In one embodiment, the subject is human.

DETAILED DESCRIPTION

The present invention is based, in part, on the discovery of novel methodologies for diagnosing neurodevelopmental disease or disorders in a fetus or neonate. Biomarkers isolated from fetal neuronal exosomes (FNEs) or neonatal neuronal exosomes (NNEs) are used as a diagnostic for diagnosing or determining a treatment for a fetal or neonatal neurodevelopmental disease or disorder.

In another aspect, the present invention is based on the discovery of novel methods for isolating fetal neuronal exosomes (FNEs) from maternal plasma as a non-invasive platform for testing aspects of fetal neurodevelopment as early as the 1st trimester. This methodology represents an important breakthrough both in understanding mechanisms of injury in an in vivo human system and in guiding and monitoring interventions seeking to promote fetal brain health.

The present invention therefore provides compositions and methods of diagnosing or prognosing a fetal or neonatal neurodevelopmental outcome in a subject, by examining relevant biomarkers and their expression.

Accordingly, in some embodiments of the invention, a method for diagnosing a fetal neurodevelopmental disease or disorder in a subject is provided. The method comprises a) providing a biological sample from the subject; b) isolating exosomes from the biological sample; c) analyzing the exosomes with an assay that specifically detects at least one biomarker of the invention in the isolated exosomes; d) comparing the subject biomarker profile with a control biomarker profile wherein a statistically significant difference between the subject biomarker profile and the control biomarker profile is indicative of a fetal neurodevelopmental disease or disorder; and e) effectuating a treatment regimen based thereon.

In one embodiment the subject is an in utero fetus. In one embodiment, the biomarker is found in an exosome isolated from a biological sample of the subject. In one embodiment, the exosome is a fetal neuronal exosome. In one embodiment, the fetal neuronal exosome is isolated from a maternal biological sample, preferably maternal plasma. In one embodiment, the fetal neuronal exosome is isolated from plasma. In some embodiments the biological sample is provided during a first trimester of gestation.

In one embodiment the subject is an in infant. In one embodiment the subject is an in neonate. In one embodiment, the biomarker is found in an exosome isolated from a biological sample of the subject. In one embodiment, the exosome is a neonatal exosome. In one embodiment, the neonatal exosome is isolated from plasma. In some embodiments the biological sample is provided within 1 day of birth. In some embodiments the biological sample is provided within 1 week of birth. In some embodiments the biological sample is provided within 4 weeks of birth.

In one embodiment, biomarker expression includes transcription into messenger RNA (mRNA) and translation into protein, as well as transcription into types of RNA such as transfer RNA (tRNA) and ribosomal RNA (rRNA) that are not translated into protein. In one embodiment, the biomarker includes microRNA (miRNA). In another embodiment the biomarker includes phosphorylation of a protein. In yet another embodiment, the biomarker includes a combination of mRNA, protein, miRNA, and protein phosphorylation.

In one embodiment, the invention provides a biomarker for the detection of fetal neurodevelopmental disease or disorder. In some embodiments, the biomarker includes, but is not limited to, CD81, Human Sonic Hedgehog, type 1 pregnancy specific β-1-glycoprotein (PSG-1), heat shock factor 1 (HSF1), B-cell lymphoma-extra large mitochondrial membrane protein (Bcl-XL), restriction element-1 silencing transcription factor (REST), Synaptophysin, GAP-43, Synaptotagmin, Synaptopodin, Stargazin, neuron-specific (NS)-enolase, neurogranulin, Insulin like growth factors 1 and 2, Gephyrin, Clic4, Netrin 1, 3 and 4, Neuroligans 1-3, Anchored Netrin G1 and G2, Thy-1, N-cadherin, Eph receptors, Ephrin A and B ligands, Neurexin, Reelin, Follistatin, Noggin, Chordin, FGF, SMARCC2, ARID1B, pASD, TBR1, POGZ, CHD8, DYRK1A, SCN2A, Glial fibrillary acidic protein, SB-100, Activin A, Creatinine Kinase BB, HSP70, Interleukin 1β, TNFα, BDNF, Ubiquitin CHL1, Lingo-1, MBP, 04, CNPase, MAG, PLP, NG2, Olig1-3, WAVE-1, PPARα, TEFB, HIF-1, PGC-1α, PPARγ, SREBP-1, Glucose transporters (Glut 1, 3), Somatostatin, Ghrelin, Orexin, Activated Caspases, Cytochrome c, C1q, ASCL1, NTF3, OLIG2, SOX2, ABL1, BAG4, BIK, CASP7, CDKN1A, CIDEA, CIDEB, CRADD, DAPK1, FAS, FASLG, GCH1, SOD2, TNFRSF10B, TNFRSF11B, TP53, TRAF4, YWHAE, miRNA9, miRNA335, miRNA153, miRNA21, miRNA210, miRNA34a, miRNA451, miRNA874, miRNA124, miRNA125, miRNA132, miRNA134, miRNA138, miRNA106, miRNA128, miRNA140, miRNA146, miRNA148, miRNA15, miRNA181, miRNA193, miRNA212, miRNA27, miRNA320, miRNA381, miRNA431, miRNA432, miRNA484, miRNA539, miRNA652, miRNA7, miRNA93, miRNA95, miRNA133, miRNA433, miRNA542, phosphorylation of S6K1Thr389, phosphorylation of 4E-BP1 Thr37, phosphorylation of 4E-BP1 Thr49, phosphorylation of 4E-BP1 Ser65, Synaptopodin (SYNPO), neurogranin, morphine receptor (MU) and any combination thereof.

In one embodiment, biomarker expression includes transcription into messenger RNA (mRNA) and translation into protein, as well as transcription into types of RNA such as transfer RNA (tRNA) and ribosomal RNA (rRNA) that are not translated into protein. In one embodiment, the mRNA or protein biomarker includes, but is not limited to CD81, Human Sonic Hedgehog, type 1 pregnancy specific β-1-glycoprotein (PSG-1), heat shock factor 1 (HSF1), B-cell lymphoma-extra large mitochondrial membrane protein (Bcl-XL), restriction element-1 silencing transcription factor (REST), Synaptophysin, GAP-43, Synaptotagmin, Synaptopodin, Stargazin, neuron-specific (NS)-enolase, neurogranulin, Insulin like growth factors 1 and 2, Gephyrin, Clic4, Netrin 1, 3 and 4, Neuroligans 1-3, Anchored Netrin G1 and G2, Thy-1, N-cadherin, Eph receptors, Ephrin A and B ligands, Neurexin, Reelin, Follistatin, Noggin, Chordin, FGF, SMARCC2, ARID1B, pASD, TBR1, POGZ, CHD8, DYRK1A, SCN2A, Glial fibrillary acidic protein, SB-100, Activin A, Creatinine Kinase BB, HSP70, Interleukin 1β, TNFα, BDNF, Ubiquitin CHL1, Lingo-1, MBP, 04, CNPase, MAG, PLP, NG2, Olig1-3, WAVE-1, PPARα, TEFB, HIF-1, PGC-1α, PPARγ, SREBP-1, Glucose transporters (Glut 1, 3), Somatostatin, Ghrelin, Orexin, Activated Caspases, Cytochrome c, C1q, ASCL1, NTF3, OLIG2, SOX2, ABL1, BAG4, BIK, CASP7, CDKN1A, CIDEA, CIDEB, CRADD, DAPK1, FAS, FASLG, GCH1, SOD2, TNFRSF10B, TNFRSF11B, TP53, TRAF4, Synaptopodin (SYNPO) neurogranin, morphine receptor (MU), and YWHAE.

In another embodiment, the biomarker includes a modification of a protein, for example protein phosphorylation, SUMOylation, glycosylation, and the like. In one embodiment, the biomarker includes phosphorylation of a protein. In some embodiments, the biomarker includes the phosphorylation of S6K1 or 4E-BP1. In another embodiment, the biomarker includes phosphorylation of 4E-BP1 Thr49, phosphorylation of 4E-BP1 Ser65 and any combination thereof.

In one embodiment, the biomarker is a microRNA (miRNA) biomarker. In some embodiments, the biomarker includes miRNA9, miRNA335, miRNA153, miRNA21, miRNA210, miRNA34a, miRNA451, miRNA874, miRNA124, miRNA125, miRNA132, miRNA134, miRNA138, miRNA106, miRNA128, miRNA140, miRNA146, miRNA148, miRNA15, miRNA181, miRNA193, miRNA212, miRNA27, miRNA320, miRNA381, miRNA431, miRNA432, miRNA484, miRNA539, miRNA652, miRNA7, miRNA93, miRNA95, miRNA133, miRNA433, miRNA542 and any combination thereof. In one embodiment, the miRNA is detected by mass spectroscopy, PCR microarray, thermal sequencing, capillary array sequencing, solid phase sequencing, and the like.

In one embodiment, the biomarker types comprise mRNA biomarkers. In one embodiment, the mRNA is detected by mass spectroscopy, PCR microarray, thermal sequencing, capillary array sequencing, solid phase sequencing, and the like.

In another embodiment, the biomarker types comprise polypeptide biomarkers. In one embodiment, the polypeptide is detected by ELISA, Western blot, flow cytometry, immunofluorescence, immunohistochemistry, mass spectroscopy, and the like.

In one embodiment, the fetal neurodevelopmental disease or disorder includes, but is not limited to, fetal alcohol syndrome (FAS), autism, attention deficit hyperactivity disorder (ADHD), hypoxic ischemic encephalopathy, congenital cytomegalovirus (CMV) infection, zika virus infection, neonatal abstinence syndrome (NAS), and cerebral palsy.

In some embodiments, the level of the biomarker is increased at a statistically significant amount when compared with the level of the biomarker of the comparator control. In other embodiments, is decreased at a statistically significant amount when compared with the level of the biomarker of the comparator control. In some embodiments, the comparator control is the level of the biomarker in the biological sample of a healthy subject. In other embodiments, the comparator control is a positive control, a negative control, a historical control, a historical norm, or the level of a reference molecule in the biological sample.

In some embodiments, a method for isolating FNEs is provided. The method comprises a) obtaining a biological sample from a pregnant subject; b) isolating a total exosome population from the biological sample; c) incubating the total exosome population with a biotinylated anti-human antibody; d) precipitating the biotinylated anti-human antibody with streptavidin resin; and e) collecting a pellet formed by the precipitating of the biotinylated anti-human antibody containing the FNE. In some embodiments, the biological sample is a maternal plasma sample. In some embodiments, the biotinylated anti-human antibody is an biotinylated anti-human antibody against a protein, wherein the protein includes, but is not limited to, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, and Vesicular Glutamate T 1-3, Glutamate Transporter, CAD 65. In some embodiments, the biotinylated anti-human antibody is a biotinylated anti-human Contactin-2/TAG1 antibody.

In various embodiments, the invention provides a kit for diagnosing a fetal neurodevelopmental disease or disorder. The kit comprises reagent for measuring the level of a biomarker in exosomes isolated from a biological sample of the subject. In some embodiments, the exosome is a fetal neural exosome.

Definitions

Unless defined otherwise, all technical and scientific terms used herein have the same meaning as commonly understood by one of ordinary skill in the art to which the invention pertains. Any methods and materials similar or equivalent to those described herein can be used in the practice for testing of the present invention. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in any cell such as a prokaryotic cell, a virus, or a eukaryotic cell (including transgenic animals); (2) a structural gene or polynucleotide sequence, which codes for the desired protein; and (3) a 3' nontranslated region, which typically causes the termination of transcription and the polyadenylation of the 3' region of the RNA sequence. Each of these elements is operably linked.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "amplification" refers to the operation by which the number of copies of a target nucleotide sequence present in a sample is multiplied.

By the term "applicator," as the term is used herein, is meant any device including, but not limited to, a hypodermic syringe, a pipette, an iontophoresis device, a patch, and the like, for administering the compositions of the invention to a subject.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the term "marker" or "biomarker" is meant to include a parameter which is useful according to this invention for determining the presence and/or severity of diabetes.

The level of a marker or biomarker "significantly" differs from the level of the marker or biomarker in a reference sample if the level of the marker in a sample from the patient differs from the level in a sample from the reference subject by an amount greater than the standard error of the assay employed to assess the marker, and preferably at least 10%, and more preferably 25%, 50%, 75%, or 100%.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

A "disease" is a state of health of an animal wherein the animal cannot maintain homeostasis, and wherein if the disease is not ameliorated then the animal's health continues to deteriorate.

"Fetal neurodevelopmental disease or disorder," as used herein is any neurologic condition or state resulting from abnormal formation or function of the brain, neurons, neurologic connections or neurologic function that originated while the fetus/neonate/child or adult was inside the uterus.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute or relative amount or concentration of the biomarker in the sample.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "providing a prognosis" refers to providing a prediction of the probable course and disease or disorder of a fetal neurodevelopmental disease or disorder, including prediction of severity, affect on the fetus, etc. The methods can also be used to devise a suitable therapeutic plan.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual, including but is not limited to organ, tissue, exosome, blood, plasma, saliva, urine and other body fluid. The biological sample may contain any biological material suitable for detecting the desired biomarkers, and may comprise cellular and/or non-cellular material obtained from the individual.

"Standard control value" as used herein refers to a predetermined amount of a particular protein or nucleic acid that is detectable in a biological sample, for example, blood, either in whole blood or in blood supernatant. The standard control value is suitable for the use of a method of the present invention, in order for comparing the amount of a protein or nucleic acid of interest that is present in a biological sample. An established sample serving as a standard control provides an average amount of the protein or nucleic acid of interest in the biological that is typical for an average, healthy person of reasonably matched background, e.g., gender, age, ethnicity, and medical history. A standard control value may vary depending on the protein or nucleic acid of interest and the nature of the sample (e.g., whole blood or supernatant).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based, in part, on the unexpected identification of biological sample-based biomarkers that, when present at altered levels, can identify fetal neurodevelopmental diseases or disorders (e.g., FAS) in an in utero fetus or neonatal neurodevelopmental diseases or disorders. In one embodiment, the biomarker is detected in fetal neuronal exosomes isolated from plasma obtained from the gestational carrier of the fetal subject. In one embodiment, the biomarker is detected in neonatal neuronal exosomes isolated from plasma obtained from a neonatal subject. In some embodiments, a change in biomarker expression relative to a comparative control is associated with a fetal neurodevelopmental disease or disorder. Thus, the invention relates to compositions and methods useful for the diagnosis, assessment, and characterization of fetal neurodevelopmental diseases or disorders in a fetal subject in need thereof, based upon the expression level of at least one biomarker found in fetal neuronal exosomes. In some embodiments, a change in biomarker expression relative to a comparative control is associated with a neonatal neurodevelopmental disease or disorder. Accordingly, the invention also relates to compositions and methods useful for the diagnosis, assessment, and characterization of neonatal neurodevelopmental diseases or disorders in a neonatal subject in need thereof, based upon the expression level of at least one biomarker found in neonatal neuronal exosomes.

Exemplary neurodevelopmental diseases and disorders, which can be identified by the present invention, include, but is not limited to, fetal alcohol syndrome (FAS), deficits due to maternal medication or drug use, autism, attention deficit hyperactivity disorder (ADHD) depression, schizophrenia, epilepsy, hypoxic ischemic encephalopathy, congenital cytomegalovirus (CMV) infection, zika virus infection, neonatal abstinence syndrome (NAS), and cerebral palsy. In some embodiments, the biomarkers identify a decreased threshold or increased risk for some later onset neurologic diseases such as Alzheimer's disease and Parkinson's disease.

In some embodiments, the biomarker associated with a fetal neurodevelopmental disease or disorder is CD81, Human Sonic Hedgehog, type 1 pregnancy specific β-1-glycoprotein (PSG-1), heat shock factor 1 (HSF1), B-cell lymphoma-extra large mitochondrial membrane protein (Bcl-XL), restriction element-1 silencing transcription factor (REST), Synaptophysin, GAP-43, Synaptotagmin, Synaptopodin, Stargazin, neuron-specific (NS)-enolase, neurogranulin, Insulin like growth factors 1 and 2, Gephyrin, Clic4, Netrin 1, 3 and 4, Neuroligans 1-3, Anchored Netrin G1 and G2, Thy-1, N-cadherin, Eph receptors, Ephrin A and B ligands, Neurexin, Reelin, Follistatin, Noggin, Chordin, FGF, SMARCC2, ARID1B, pASD, TBR1, POGZ, CHD8, DYRK1A, SCN2A, Glial fibrillary acidic protein, SB-100, Activin A, Creatinine Kinase BB, HSP70, Interleukin 1β, TNFα, BDNF, Ubiquitin CHL1, Lingo-1, MBP, O4, CNPase, MAG, PLP, NG2, Olig1-3, WAVE-1, PPARα, TEFB, HIF-1, PGC-1α, PPARγ, SREBP-1, Glucose transporters (Glut 1, 3), Somatostatin, Ghrelin, Orexin, Activated Caspases, Cytochrome c, C1q, ASCL1, NTF3, OLIG2, SOX2, ABL1, BAG4, BIK, CASP7, CDKN1A, CIDEA, CIDEB, CRADD, DAPK1, FAS, FASLG, GCH1, SOD2, TNFRSF10B, TNFRSF11B, TP53, TRAF4, YWHAE, miRNA9, miRNA335, miRNA153, miRNA21, miRNA210, miRNA34a, miRNA451, miRNA874, miRNA124, miRNA125, miRNA132, miRNA134, miRNA138, miRNA106, miRNA128, miRNA140, miRNA146, miRNA148, miRNA15, miRNA181, miRNA193, miRNA212, miRNA27, miRNA320, miRNA381, miRNA431, miRNA432, miRNA484, miRNA539, miRNA652, miRNA7, miRNA93, miRNA95, miRNA133, miRNA433, miRNA542, phosphorylation of S6K1Thr389, phosphorylation of 4E-BP1 Thr37, phosphorylation of 4E-BP1 Thr49, phosphorylation of 4E-BP1 Ser65, Synaptopodin (SYNPO), neurogranin, morphine receptor (MU) and any combination thereof.

TABLE 1

| Neurodevelopmental Biomarkers Measured in FNEs | |
|---|---|
| Gene Products/Proteins (measure by protein or mRNA expression) | Stargazin, neuron-specific (NS)-enolase, neurogranulin, Insulin like growth factors 1 and 2, Gephyrin, Clic4, Netrin 1, 3 and 4, Neuroligans 1-3, Anchored Netrin G1 and G2, Thy-1, N-cadherin, Eph receptors, Ephrin A and B ligands, Neurexin, Reelin, Follistatin, Noggin, Chordin, FGF, SMARCC2, ARID1B, pASD, TBR1, POGZ, CHD8, DYRK1A, SCN2A, Glial fibrillary acidic protein, SB-100, Activin A, Creatinine Kinase BB, HSP70, Interleukin 1β, TNFα, BDNF, Ubiquitin CHL1, Lingo-1, Synaptopodin (SYNPO), neurogranin, morphine receptor (MU) |
| Myelination | MBP, O4, CNPase, MAG, PLP, NG2, Olig1-3, WAVE-1 |
| microRNAs | 9, 335, 153, 21, 210, 34a, 451, 874, 124, 125, 132, |

TABLE 1-continued

| Neurodevelopmental Biomarkers Measured in FNEs | |
|---|---|
| (miRNAs, with subregions) | 134, 138, 106, 128, 140, 146, 148, 15, 181, 193, 212, 27, 320, 381, 431, 432, 484, 539, 652, 7, 93, 95, 133, 433, 542 |
| mTOR pathway | Phosphorylation of S6K1 (on Thr389), 4E - BP1 (on Thr37, Thr46, and Ser65) and Akt (on Ser473). PPARα, TEFB, HIF-1, PGC-1α, PPARγ, SREBP-1 |
| Metabolism | Glucose transporters (Glut 1, 3), Somatostatin, Ghrelin, Orexin |
| Apoptosis/Cell Fate | Activated Caspases, Cytochrome c, C1q, ASCL1, NTF3, OLIG2, SOX2, ABL1, BAG4, BIK, CASP7, CDKN1A, CIDEA, CIDEB, CRADD, DAPK1, FAS, FASLG, GCH1, SOD2, TNFRSF10B, TNFRSF11B, TP53, TRAF4, YWHAE |

In another aspect, the present invention provides a method for isolating a fetal exosome from a biological sample of a pregnant subject. In one embodiment, the fetal exosome is a fetal neuronal exosome. In another embodiment, the biological sample of the pregnant subject is maternal plasma.

Isolation of FNEs

In certain embodiments, the present invention relates to the detection and use of the levels of biomarkers in a biological sample of a gestational carrier to diagnose or prognose a fetal neurodevelopmental disease or disorder in an in utero fetal subject. In some embodiments, the biological sample of the invention can be obtained from blood. In some embodiments, about 1-10 mL of blood is drawn from a gestational carrier. In other embodiments, about 10-50 mL of blood is drawn from a gestational carrier. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues. Samples can be enriched for vesicles through positive selection, negative selection, or a combination of positive and negative selection. In some embodiments, vesicles are directly captured. In other embodiments, blood cells are captured and vesicles are collected from the remaining biological samples. In some embodiments, the vesicles enriched in the biological samples are exosomes, microparticles, microvesicles, nanosomes, extracellular vesicles, or ectosomes. In some embodiments, the vesicles enriched in the biological samples are neuron-derived exosomes, astrocyte-derived exosomes, oliogodendrocyte-derived exosomes, and microglia-derived exosomes.

Samples can also be enriched for vesicles based on differences in the biochemical properties of vesicles. For example, samples can be enriched for vesicles based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. Samples can also be enriched for vesicles based on other biochemical properties known in the art. For example, samples can be enriched for vesicles based on pH or motility. Further, in some embodiments, more than one method is used to enrich for vesicles. In other embodiments, samples are enriched for vesicles using antibodies, ligands, or soluble receptors.

In other embodiments, surface markers are used to positively enrich vesicles in the sample. In some embodiments, the vesicles are exosomes, microparticles, microvesicles, nanosomes, extracellular vesicles, or ectosomes. In other embodiments, surface markers are used to enrich for exosomes. For example, markers including, but not limited to contactin-2/TAG1, NCAM, CD171, CD9, CD63, CD81, diverse neuron or astrocyte adhesive proteins, microglial CD18/11, CD3, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, Vesicular Glutamate T 1-3, Glutamate Transporter, or CAD 65 can be used to enrich various exosome populations In some embodiments, cell surface markers that are not found on vesicles populations are used to negatively enrich vesicles by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in vesicles. Cell surface markers may include antibodies against cell surface antigens that are preferentially expressed on exosomes (e.g., Contactin-2/TAG1). In some embodiments, the cell surface marker is a neuron-derived exosome surface marker, including, for example, Contactin-2/TAG1, NCAM or CD171.

In some embodiments, a monoclonal Contactin-2/TAG1, NCAM, CD9, CD63, CD81 CD171, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, Vesicular Glutamate T 1-3, Glutamate Transporter, or CAD 65 antibody is used to enrich or isolate exosomes from the sample. In certain aspects, the Contactin-2/TAG1, NCAM, CD9, CD63, CD81, CD171, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, Vesicular Glutamate T 1-3, Glutamate Transporter, or CAD 65 antibody is biotinylated. In this embodiment, biotinylated Contactin-2/TAG1, NCAM or CD171 antibody can form an antibody-exosome complex that can be subsequently isolated using streptavidin-agarose resin or beads. In other embodiments, the Contactin-2/TAG1, NCAM, CD9, CD63, CD81, CD171, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, Vesicular Glutamate T 1-3, Glutamate Transporter, or CAD 65 antibody is a monoclonal anti-human Contactin-2/TAG1, NCAM, CD9, CD63, CD81, CD171, S100, GLAST (EAAT), HES-1, Notch1, Doublecortin, NeuN, Internexin α, NeuN, Semaphorin ligands, VAMP, Zenon, CD-90, Laminin-1, NAP 22, L1 NAM, Nestin, Sox2, RC2, BLBP, EMR1, MSR1, CD11b, CD45, CD68, GFP, SCIP analogs, Tyro 3, KA1 analogs, CALB1, Lhx1/5, RGS8, Pcp2, GDNF, LRP6 (excitatory), TorsinA, Parkin, Dopamine Transporter (DAT), Serotonin Transporter (SERT), Vesicular Actelycholine Transporter, Choline transporter, Vesicular GABA Transporter, GABA Transporters 1-3, DARPP-32, Vesicular Glutamate T 1-3, Glutamate Transporter, or CAD 65 antibody.

In some embodiments, enriched vesicles from the biological sample are subsequently enriched for a specific type of vesicle. For example, the biological sample is enriched for exosomes and then the enriched exosomes are subsequently enriched for neural-derived exosomes. In some embodiments, the biological sample is enriched for exosomes and then the enriched exosomes are subsequently enriched for fetal neural exosomes. In some embodiments, the biological sample is enriched for exosomes and then the enriched exosomes are subsequently enriched for neural-derived exosomes, and then the enriched neural-derived exosomes are enriched for fetal neural exosomes. In some embodiments, the biological sample is enriched for individual neural cell sources of vesicles. In certain aspects, the neural cell sources of vesicles are microglia, neurons, or astrocytes.

In other embodiments, fetal exosomes are isolated from a biological sample comprising: obtaining a biological sample from a pregnant subject, isolating a total exosome population from the biological sample, contact the total exosome population with an agent, wherein the agent comprises at least a moiety that binds the fetal exosome and a label, contacting the agent with a substrate comprising a moiety that binds a the label to form a complex consisting of the substrate, the agent and the fetal exosome, and isolating the complex. In some embodiments, the fetal exosome is a fetal neural exosome. In another embodiment, the agent is an antibody. In a specific embodiment, the antibody is a contactin-2/TAG1 antibody. In yet another embodiment, the label is biotin and the substrate is streptavidin.

TABLE 2

Antibodies for Purifying Subpopulations or Anatomic Regions from Fetally Derived Neuronal Exosomes

| | |
|---|---|
| Astrocyt | S100, GLAST (EAAT), HES-1, Notch1 |
| Neurons | Doublecortin, NeuN, Internexin α, NeuN, Semaphorin ligands, VAMP, Zenon, CD-90, Laminin-1, NAP 22, L1 NAM, |
| Neural Stem Cells | Nestin, Sox2 |
| Microglia | RC2, BLBP, EMR1, MSR1, CD11b, CD45, CD68 |
| Hippocampus | GFP, SCIP analogs, Tyro 3, KA1 analogs |
| Cerebellum | CALB1, Lhx1/5, RGS8, Pcp2 |
| Forebrain | GDNF |
| Synapses | LRP6 (excitatory) |
| Dopaminergic | TorsinA, Parkin, Dopamine Transporter (DAT) |
| Seratonergic | Serotonin Transporter (SERT) |
| Cholinergic | Vesicular Actelycholine Transporter, Choline transporter |
| GABAergic | Vesicular GABA Transporter, GABA Transporters 1-3, DARPP-32 |
| Glutamatergic | Vesicular Glutamate T 1-3, Glutamate Transporter, CAD 65 |

Identifying a Marker or Biomarker

The invention includes methods for the identification of differentially expressed markers between biological samples of a subject and a comparative control.

The invention contemplates the identification of differentially expressed markers by whole genome nucleic acid microarray, to identify markers differentially expressed between the subject and the comparative control. The invention further contemplates using methods known to those skilled in the art to detect and to measure the level of differentially expressed marker expression products, such as RNA and protein, to measure the level of one or more differentially expressed marker expression products.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, miRNA, protein, protein phosphorylation and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, immunohistochemistry, microarray and functional techniques such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA and miRNA include Northern blots, slot blots, dot blots, and hybridization to an ordered array of oligonucleotides. Any method for specifically and quantitatively measuring a specific protein or mRNA, miRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

Biological samples may be of any biological tissue or fluid containing fetal neuronal exosomes. Frequently the sample will be a "clinical sample" which is a sample derived from a patient.

Controls groups may either be normal or samples from known fetal neurodevelopmental disorders. As described below, comparison of the expression patterns of the sample to be tested with those of the controls can be used to diagnose or prognose between normal and abnormal fetal neurodevelopmental diseases or disorders subjects. In some instances, the control groups are only for the purposes of establishing initial cutoffs for the assays of the invention. Therefore, in some instances, the systems and methods of the invention can diagnose or prognose between normal abnormal fetal neurodevelopmental diseases or disorders in subjects without the need to compare with a control group.

Methods of Diagnosis

The present invention relates to the identification of biomarkers associated with fetal neurodevelopmental diseases or disorders. Accordingly, the present invention features methods for identifying subjects who are at risk of developing abnormal fetal neurodevelopmental diseases or disorders, including those subjects who are asymptomatic or only exhibit non-specific indicators of abnormal fetal neurodevelopmental diseases or disorders by detection of the biomarkers disclosed herein.

The invention provides improved diagnosis of abnormal fetal neurodevelopmental diseases or disorders. The risk of having an abnormal fetal neurodevelopmental outcome can be assessed by measuring one or more of the biomarkers described herein, and comparing the measured values to reference or index values. Such a comparison can be undertaken with mathematical algorithms or formula in order to combine information from results of multiple individual biomarkers and other parameters into a single measurement or index.

The biomarkers of the present invention can thus be used to generate a biomarker profile or signature of subjects: (i) who do not have and are not expected to develop abnormal fetal neurodevelopmental outcomes and/or (ii) who have or expected to develop abnormal fetal neurodevelopmental outcomes. The biomarker profile of a subject can be compared to a predetermined or reference biomarker profile to diagnose or identify subjects at risk for abnormal fetal neurodevelopmental outcomes. Data concerning the biomarkers of the present invention can also be combined or correlated with other data or test results, such as, without limitation, measurements of clinical parameters or other algorithms for abnormal fetal neurodevelopmental outcomes. Other data includes maternal age at the time of gestation, genetic variants, alcohol use during pregnancy, exposures the drugs or medications, exposure to adverse environmental conditions or toxins, exposure to in-utero inflammation or infection, exposure to fetal hyperthermia or hypoxia, and use of interventions specifically designed to improve neurodevelopmental outcomes. The machine-readable media can also comprise subject information such as medical history and any relevant family history.

In various embodiments, methods are disclosed herein that may be of use to determine whether a subject has an abnormal fetal neurodevelopmental outcome. In some embodiments, these methods may utilize a biological sample, for the detection of one or more markers of the invention in the sample.

In one embodiment, the invention provides a biomarker for the detection of abnormal fetal neurodevelopmental outcomes. In one embodiment, the biomarker for the detection of abnormal fetal neurodevelopmental outcomes can be, but is not limited to CD81, Sonic Hedgehog, PSG-1, HSF1, Bcl-XL, and Synaptophysin, GAP-43, Synaptotagmin, Stargazin, neuron-specific (NS)-enolase, Synaptopodin (SYNPO), neurogranin, morphine receptor (MU) and REST.

In one embodiment, the method comprises detecting one or more markers in a biological sample of the subject. In some embodiments, the biological sample is plasma. In one embodiment, the biological sample is fetal plasma. In one embodiment, the biological sample is maternal plasma. In various embodiments, the level of one or more of markers of the invention in the biological sample of the subject is compared with the level of a corresponding biomarker in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In various embodiments, the subject is a human subject. In some embodiments, the subject is a fetus.

Information obtained from the methods of the invention described herein can be used alone, or in combination with other information (e.g., disease status, disease history, vital signs, blood chemistry, etc.) from the subject or from the biological sample obtained from the subject.

In other various embodiments of the methods of the invention, the level of one or more markers of the invention is determined to be increased when the level of one or more of the markers of the invention is increased by at least 10%, by at least 20%, by at least 30%, by at least 40%, by at least 50%, by at least 60%, by at least 70%, by at least 80%, by at least 90%, or by at least 100%, when compared to with a comparator control. In the methods of the invention, a biological sample from a subject is assessed for the level of one or more of the markers of the invention in the biological sample obtained from the patient. The level of one or more of the markers of the invention in the biological sample can be determined by assessing the amount of polypeptide of one or more of the biomarkers of the invention in the biological sample, the amount of mRNA of one or more of the biomarkers of the invention in the biological sample, the amount of enzymatic activity of one or more of the biomarkers of the invention in the biological sample, or a combination thereof.

Detecting a Biomarker

In one embodiment, the invention includes detecting a biomarker mRNA in an exosome, wherein the bodily fluid is maternal plasma and the exosome are fetal neural exosomes. Detecting exosomal biomarkers is in particular performed in a portion of maternal plasma.

In one embodiment, detecting biomarkers is performed in a maternal bodily fluid, plasma, urine, or saliva, that meets the demands of an inexpensive, non-invasive and accessible bodily fluid to act as an ideal medium for investigative analysis.

Biomarkers generally can be measured and detected through a variety of assays, methods and detection systems known to one of skill in the art. Various methods include but are not limited to refractive index spectroscopy (RI), ultraviolet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In some embodiments, the nucleic acid form is mRNA. In various embodiments, measurements of protein biomarkers are used in conjunction with measurements of nucleic acid biomarkers.

Methods for detecting mRNA and miRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of markers. In another embodiment, the method comprises a set of compatible analytical strategies for multiplex measurements of markers and/or metabolites in a biological sample.

Kits

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample. In another embodiment, the kit comprises components useful for the quantification of a desired polypeptide in a biological sample. In a further embodiment, the kit comprises components useful for the assessment of the activity (e.g., enzymatic activity, substrate binding activity, etc.) of a desired polypeptide in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

In certain embodiments, the kit comprises a means for enriching or isolating exosomes in a biological sample. In further aspects, the means for enriching or isolating exosomes comprises reagents necessary to enrich or isolate exosomes from a biological sample. In some embodiments, the kit comprises a means for enriching fetal neural exosomes.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Fetal Neural Exosomes Obtained from Maternal Plasma

The results presented herein demonstrate novel methods for isolating fetal neural exosomes (FNEs) from maternal plasma in early pregnancy. Further, data is presented herein suggests that decreased fetal neuronal defenses can be detected following in utero exposure to the known fetal neurotoxin ethanol as early as the 1st trimester. This methodology represents an important breakthrough both in understanding mechanisms of injury in an in vivo human system and in guiding and monitoring interventions seeking to promote fetal brain health.

The materials and methods employed in the experiments disclosed herein are now described.

Patient Groups and Blood Sampling

Under an institutional review board approved protocol, plasmas were obtained from healthy pregnant women in the 1st or 2nd trimester (HP, n=20), from gestational age matched pregnancies with current heavy EtOH use (FAS, n=10) and from non-pregnant controls (n=16). Twenty ml of venous blood were drawn into 1 ml of saline with EDTA or heparin, incubated for 10 min at room temperature and centrifuged for 15 min at 2,500×g. Plasma was stored in 0.5 ml aliquots at −80° C.

Isolation of Fetal Neural Exosomes from Plasma for Extraction and ELISA Quantification of Exosomal Proteins 250 µL of plasma were incubated with 100 µL of thromboplastin-D (Fisher Scientific, Inc., Hanover Park, Ill.) and then cocktails of protease and phosphatase inhibitors as described (Kapogiannis et al., 2015, Faseb J 29:589-96; Fiandaca et al., 2015, Alzheimers Dement 11:600-7). After centrifugation, supernates were incubated with exosome precipitation solution (EXOQ; System Biosciences, Inc., Mountainview, Calif.), resultant suspensions centrifuged at 1,500×g for 30 min at 4° C., and pellets re-suspended in 400 µL of distilled water with inhibitor cocktails for immunochemical enrichment of exosomes (Kapogiannis et al., 2015, Faseb J 29:589-96; Fiandaca et al., 2015, Alzheimers Dement 11:600-7). To isolate exosomes from fetal neural sources, total exosome suspensions were incubated for 90 min at 20° C. with 50 µL of 3% BSA (Thermo Scientific, Inc.) containing 2 µg of mouse monoclonal IgG1 anti-human Contactin-2/TAG1 antibody (clone 372913, R&D Systems, Inc., Minneapolis, Minn.), that had been biotinylated (EZ-Link sulfo-NHS-biotin System, Thermo Scientific, Inc.). Then 10 µl of Streptavidin-Plus UltraLink resin (Pierce-Thermo Scientific, Inc.) in 40 µL of 3% BSA were added and the incubation continued for 60 min at 20° C. (Goetzl et al., 2015, Neurology 85:40-7; Goetzl et al., 2015, Ann Clin Trans Neurol 2:769-73). After centrifugation at 300×g for 10 min at 4° C. and removal of supernates, pellets were re-suspended in 75 µl of 0.05 M glycine-HCl (pH 3.0), incubated at 4° C. for 10 min and re-centrifuged at 4,000×g for 10 min at 4° C. Each supernate in a new 1.7 ml Eppendorf tube was mixed with five µL of 1 M Tris-HCl (pH 8.0) and 20 µL of 3% BSA followed by addition of 0.40 ml of M-PER mammalian protein extraction reagent (Thermo Scientific, Inc.) containing protease and phosphatase inhibitors prior to storage at −80° C. For exosome counts, immunoprecipitated pellets were re-suspended in 0.25 ml of 0.05 M glycine-HCl (pH=3.0) at 4° C., suspension pH adjusted to 7.0 with 1 M Tris-HCl (pH 8.6) and exosome suspensions diluted 1:200 to permit counting in the range of $1-5 \times 10^8$/ml, with an NS500 nanoparticle tracking system (NanoSight, Amesbury, UK), as described (Fiandaca et al., 2015, Alzheimers Dement 11:600-7).

The tetraspanning exosome marker human CD81 (American Research Products-Cusabio) and neural markers neuron-specific (NS)-enolase (R&D Systems, Inc.), neurofilament light (NF-L) chain (American Research Products, Waltham, Mass.-Cusabio) and Ll-cell adhesion molecule (L1CAM) (Biomatik, Wilmington, Del.) were quantified by human-specific ELISAs according to suppliers' directions. Exosomal cargo levels of human Sonic Hedgehog (Abcam, Inc., Cambridge, Mass.), type 1 pregnancy specific β-1-glycoprotein (PSG-1) (R&D Systems, Inc.), type 1 heat-shock factor (HSF1) (Enzo Life Sciences, Inc., Farmingdale, N.Y.), B cell lymphoma-extra large (Bcl-XL) (American Research Products-Cusabio) and restriction element-1 silencing transcription factor (REST) (American Research Products-Cusabio) also were quantified by ELISAs. The mean value for all determinations of CD81 in each assay group was set at 1.00 and the relative values for each sample used to normalize their recovery.

Placental tissue was weighed and homogenized at 1 g/ml to approximate tissue fluid levels of proteins in M-PER with protease and phosphatase inhibitors using a motorized pestle system adapted to 1.5 ml Eppendorf tubes (Bel-Art, Thomas Scientific Co., Swedesboro, N.J.) for 3 min at 4° C. Homogenates were centrifuged at 2,000×g for 10 min at 4° C. and supernates were stored at −80° C. in 100 µL aliquots.

The results of the experiments presented in this Example are now described.

Contactin-2/TAG1 is a glycosylphosphatidylinositol-anchored neuronal membrane adhesion protein of the immunoglobulin superfamily that is transiently expressed in early human developmental stages to guide initial axonal connections and, in association with other proteins, promote molecular organization of myelinated nerves (Hasler et al., 1993, Eur J Biochem 211:329-39; Mortl et al., 2007, Protein Sci 16:2174-83). A monoclonal antibody specific for contactin-2 immunoabsorbed a subset of plasma exosomes, considered to be fetal neural exosomes, from physically-precipitated and resuspended total plasma exosomes of pregnant women. Counts of immunoabsorption-enriched fetal neural exosomes were a mean (n=3 in each group) of $1.04 \times 10^8$, $0.86 \times 10^8$ and $<10^7$ per ml of plasma, respectively, in healthy pregnancies, FAS pregnancies and non-pregnant control women. In contrast, counts of total neural exosomes that had been immunoabsorption-enriched with anti-L1CAM antibody, as described, (Goetzl et al., 2015, Neurology 85:40-7) were a mean (n=3 in each group) of $5.47 \times 10^8$, $4.96 \times 10^8$ and $5.22 \times 10^8$, respectively, in healthy pregnancies, FAS pregnancies and non-pregnant control women. The preliminary conclusion was that fetal neural exosomes constitute approximately 20% of the total set of neural exosomes in the plasma of women in the first/second trimester of pregnancy.

The identity of fetal neural exosomes recovered from plasma was supported by quantification of their protein markers (FIG. 1). The CD81 exosome marker level in fetal neural exosomes was similar in healthy pregnancies and FAS pregnancies, but only 3% of those values for non-pregnant control women. In contrast, total neural exosomes had mean±SEM levels of CD81 that were similar at 3845±81.7 and 4257±135 pg/ml, respectively, in healthy pregnancies and non-pregnant control women. The levels of neural markers NS-enolase, NF-light chains and L1CAM were similar in fetal neural exosomes from plasmas in healthy pregnancies and FAS pregnancies, but much lower in non-pregnant control women (FIG. 1). As the pregnancy values of neural markers in fetal neural exosomes were indistinguishable from those in four-fold greater amounts of total neural exosomes from plasmas of non-pregnant control women, neural markers appear to be more highly expressed in plasma fetal neural exosomes than the total plasma set of neural exosomes. Similarly high levels of the fetal marker Sonic Hedgehog were recovered from plasma fetal neural exosomes in healthy pregnancies and FAS pregnancies, as contrasted with much lower levels in non-pregnant control women (FIG. 1). The placental marker PSG-1 was readily quantified in placental tissue extracts, but levels in plasma fetal neural exosomes were undetectable in FAS pregnancies and non-pregnant control women, and only 1.5% of placental tissue levels in plasma fetal neural exosomes from healthy pregnancies essentially excluding placental origin of the purified exosomes.

To assess the resistance of developing fetal neurons to injuries inflicted in the FAS, levels of the heat shock transcription factor 1 (HSF1), that recruits heat-shock neuronal survival factors (Abravaya et al., 1992, Genes dev 6:1153-64; He et al., 2003, J Biol Chem 278:35465-75), B-cell lymphoma-extra large (Bcl-XL) mitochondrial membrane protein, that suppresses mitochondrial-mediated caspase activation and consequent neuronal apoptosis (Jonas et al., 2014, Front physiol 5:355-64) and restriction element-1 silencing transcription factor (REST) (Schoenherr and Anderson, 1995, Science 267:1360-3; Lu et al., 2014, Nature 507:448-54), that maintains brain levels of diverse neuronal defense factors, were quantified in plasma fetal neural exosomes (FIG. 2). Levels of all three neuronal defense proteins were significantly lower in FAS than in healthy pregnancies. REST showed the greatest differences with overlap of only one data point (FIG. 2).

Figure 4:
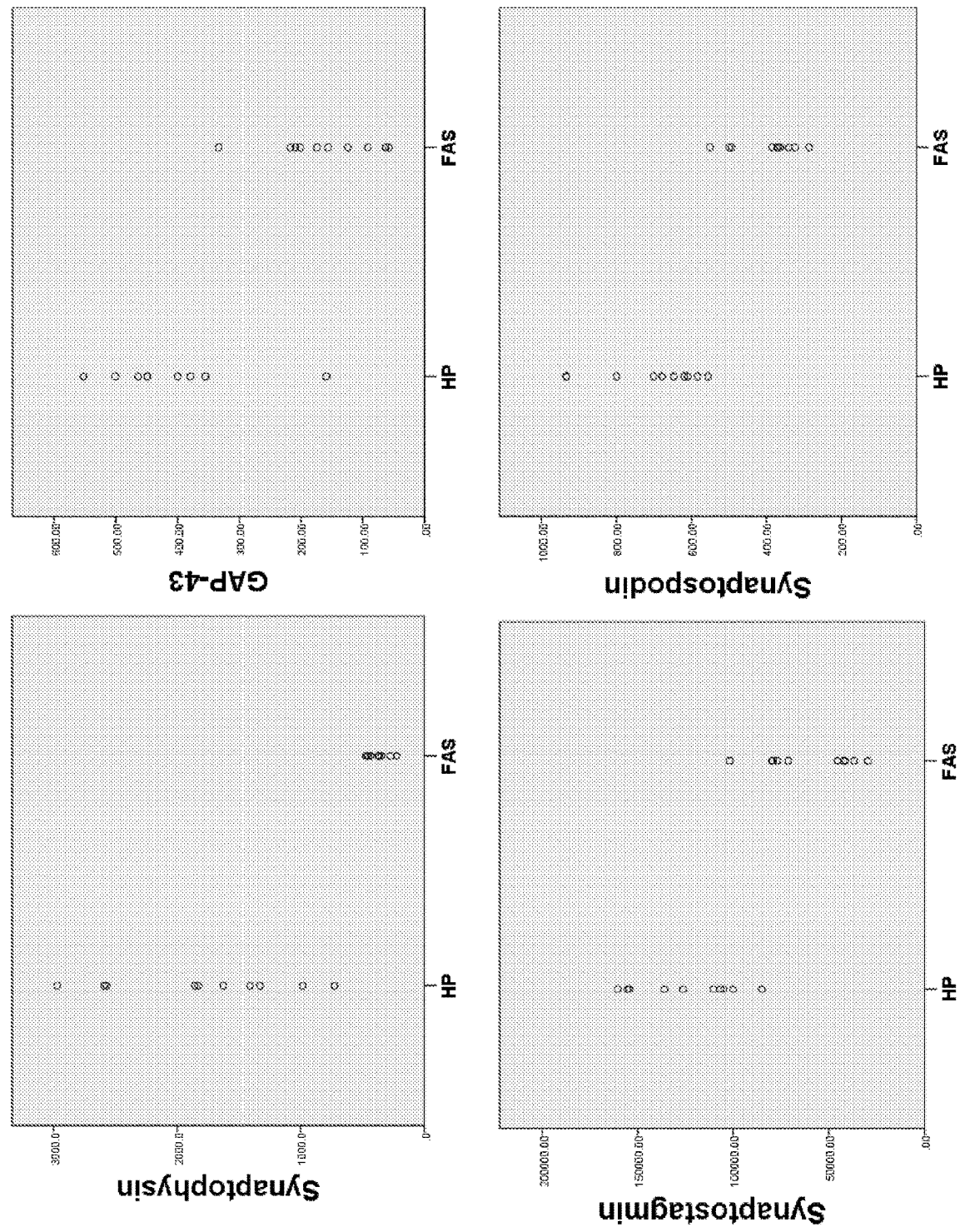
FIG. 4 depicts experimental results demonstrating low neuronal exosomal levels of synaptogenically-critical proteins in fetal alcohol syndrome compared to healthy pregnancies. Each point represent a value for a control healthy pregnancy (HP, n=10) or pregnancy with heavy alcohol exposure (FAS, n=10). The significance of differences between levels of Synaptophysin ($p<0.001$), GAP-43 ($p<0.0001$), Synaptotagmin ($p<0.0001$), Synaptopodin ($p<0.0001$) for the HP and FAS pregnancy groups was calculated by an unpaired t test.

Further, the levels of Synaptostagmin, Synaptophysin, Synaptospodin and GAP-43, synaptogenically-critical proteins, were quantified in plasma fetal neural exosomes (FIG. 3 and FIG. 4). Levels of each of these proteins were significantly lower in FAS than in healthy pregnancies.

These results suggest that FNEs purified from maternal plasma are a powerful tool to assess aspects of fetal neurodevelopment as early as the first trimester. The earliest feasible time point in gestation when the minimal mass of the fetal brain would be expected to release the smallest absolute amount of exosomes into the maternal circulation was purposefully targeted. While FNEs were essentially undetectable in non-pregnant women, the possibility that FNEs persist in the maternal circulation as do fetal cells cannot be excluded (Bianchi et al., 1996, PNAS 93:705-8). However, even if a few FNEs continue into subsequent pregnancies, the expected relatively low level of contamination is unlikely to be problematic. Finally, the data herein suggests that fetal neuronal damage can be detected non-invasively following in utero exposure to EtOH in the 1st trimester. Neuronal injury may be partially attributable to decreased resistance to diverse toxic factors as reflected in lower than normal levels of neuronal survival proteins (Cartwright and Smith, 1995, 19:378-86; Kumar et al., 2013, Brain Sci 3:941-63; Ikonomidou et al., 2000, Science 287:1056-60; Olney et al., 2002, Brain Path 12:488-98). This methodology represents an important breakthrough both in understanding mechanisms of injury in an in vivo human system and supporting findings from animal models where the validity of extrapolation to human development has not always been clear (Patten et al., 2014, front Pediatr 2:93). It is important to delineate precisely those cellular processes represented within FNE exosomes; the changing composition of FNEs across gestational age; and what aspects of disrupted neurodevelopment are detectable. This work allows for correlation of postnatal neurodevelopmental outcomes with serial non-invasive measures of in utero brain development across gestation. Ultimately, FNE based assessments may be used to guide and monitor interventions seeking to promote fetal brain health and reduce rising rates of autism, ADHD and other neurodevelopmental disorders with potential in utero contributions.

Example 2: Fetal Neuronal Exosome Morphine Receptor Levels and Maternal Opioid Use Opioid use disorder in pregnancy is common, resulting in significant neonatal morbidity and health care costs. Compared to methadone, buprenorphine is associated with less neonatal opioid requirements and shorter length of stay for neonatal abstinence syndrome (NAS). The data described herein demonstrates that methadone and buprenorphine is associated with differences in fetal brain morphine receptor (MU) levels as measured non-invasively through fetal neuronal exosomes (FNEs) isolated from maternal blood.

Maternal plasma samples were collected between 9 and 21 weeks gestation (GA). A detailed face to face questionnaire quantified maternal opioid exposure. FNEs were isolated as previously described (Example 1). MU and CD81 protein levels quantified using commercial ELISA kits and MU was normalized to CD81.

Figure 5:
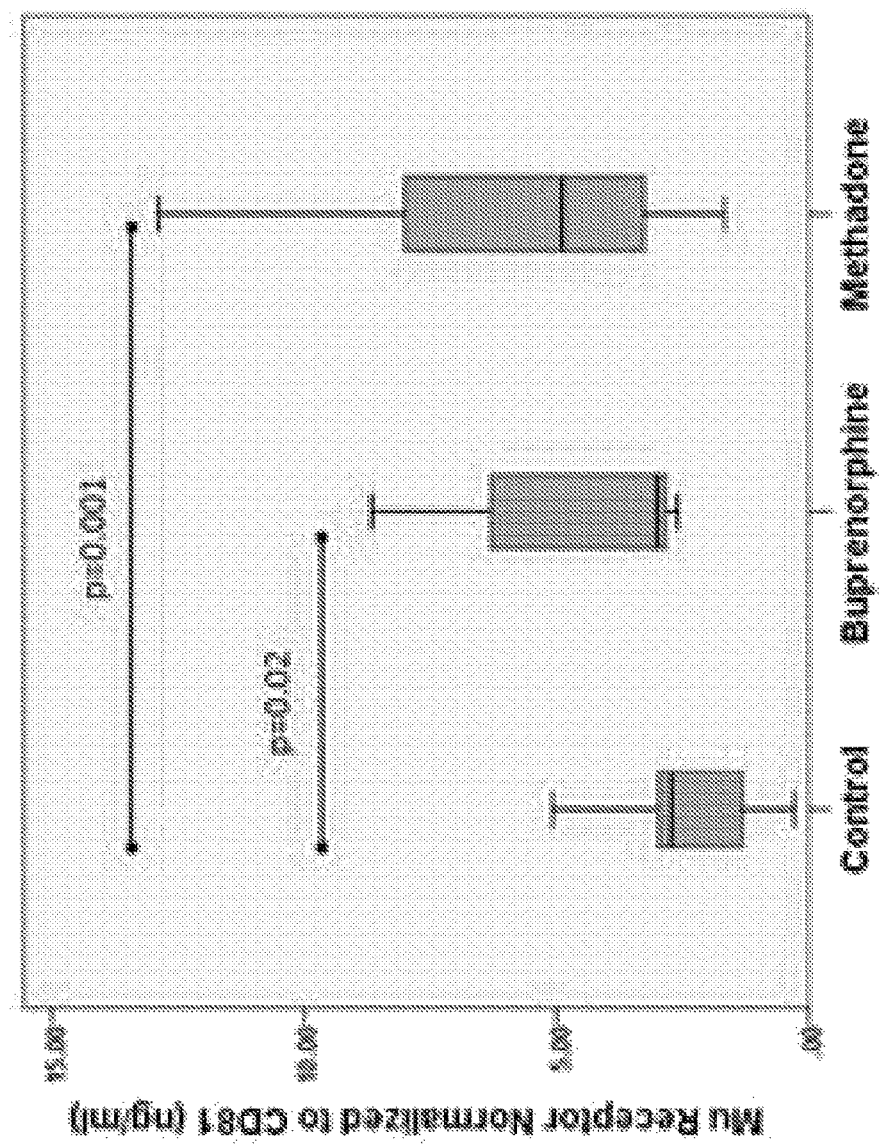
FIG. 5 depicts experimental results demonstrating that exposure to opioids increases MU levels in FNEs.

Samples were analyzed from 4 groups: control (n=19), methadone (n=10), buprenorphine (n=5) and buprenorphine/naloxone (n=6). MU was not different based on naloxone exposure, therefore the two buprenorphine groups were combined for analysis. Exposure to opioids increased MU levels in FNEs (FIG. 5). Levels appeared to be higher with methadone compared to buprenorphine but the difference was not statistically significant (p=0.25). There was no correlation between morphine equivalent dose (MED) and MU (r=0.21, p=0.36).

Down regulation of MU is expected with prolonged exposure to opioids. The unexpected finding of increased MU in FNEs suggests that neurons may down regulate MU through disposal of MU as exosome cargo. The lack of a direct relationship between MU and MED suggests that the exposure of the fetal brain to opioids is also dependent on placental and maternal factors. Although not conclusive, these data suggest that buprenorphine has a lesser effect on fetal brain MU, concordant with known clinical outcomes. Finally, these data suggest that risk of NAS may be non-invasively predicted across the course of pregnancy through MU FNE levels as a measure of MU down regulation in the fetal brain.

Example 3: Neuronal Exosome Synaptopodin: An Early Predictor of Therapeutic Response to Head Cooling Neonatal head cooling for hypoxic ischemic encephalopathy is current standard of care and is associated with some improvement in neurologic outcome. However reliable biomarkers for estimating therapeutic response are lacking. Biomarkers would be useful in identifying a subset of patients requiring additional treatment as well as aid in counseling parents.

A secondary analysis was performed on neonatal samples collected at 8, 10 and 14 hours after the initiation of therapeutic head cooling for acute encephalopathy. Neuronal exosomes were purified from plasma as previously described. Synaptopodin (SYNPO), Neural Specific Enolase (NSE), and Mitochondrial Cytochrome C Oxidase (COX IV) protein levels were quantified using standard ELISA methods. The primary study outcomes were length of stay (LOS) and discharge on seizure treatment (DCMED)

Figure 6:
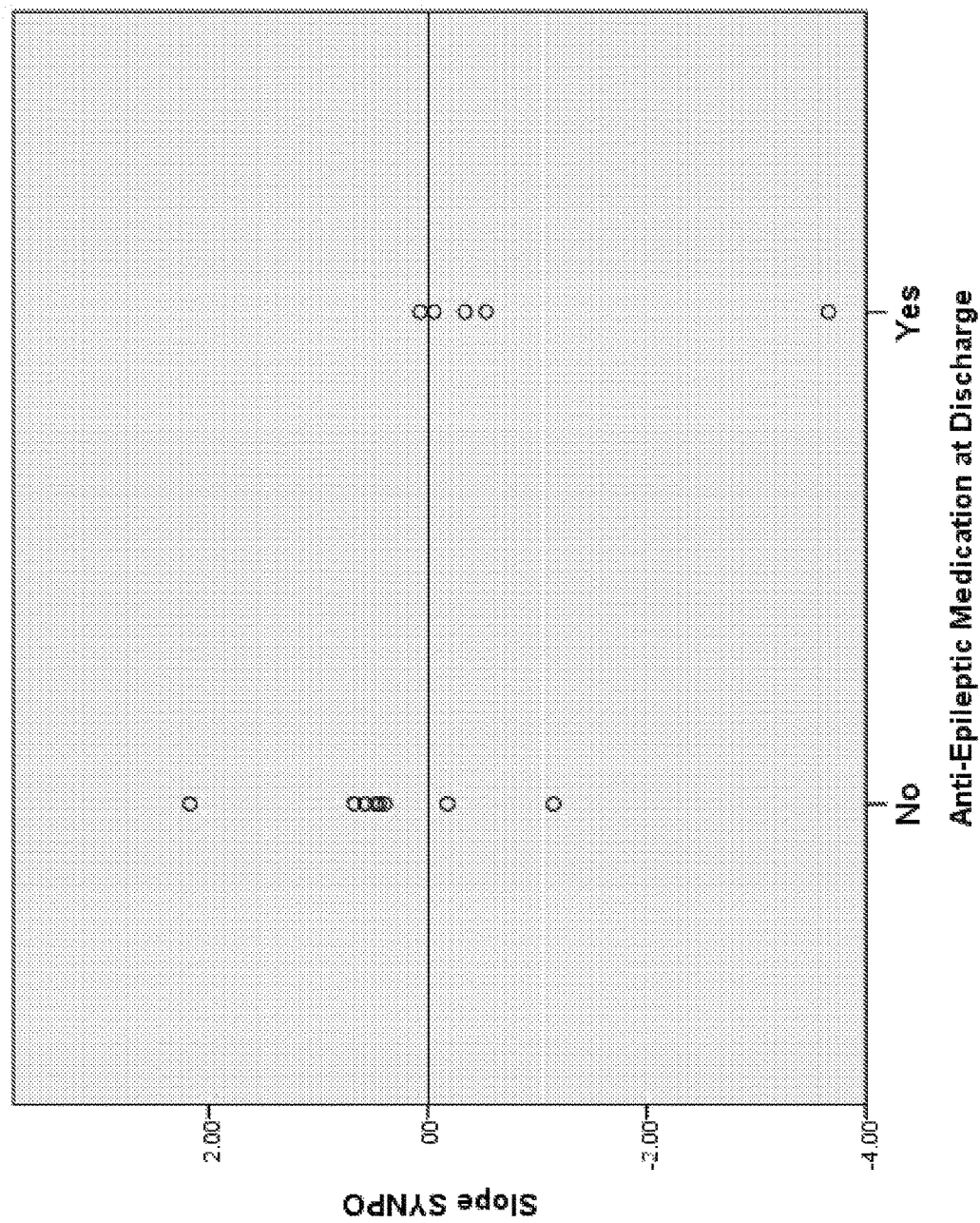
FIG. 6 depicts experimental results demonstrating that neural exosome Synaptopodin (SYNPO) slope was highly correlated with length of stay (LOS) ($-0.91$, $p<0.001$) and SYNPO slope predicted discharge on seizure treatment (DCMED).

13 subjects were included. The slope of change for biomarker levels was calculated between 8 and 14 hours. Among short term clinical markers (5 minute APGAR, cord pH or Base Excess), only pH was weakly correlated with LOS (r=−0.54, p=0.05) and none with DCMED. In contrast, neural exosome SYNPO slope was highly correlated with LOS (−0.91, p<0.001) and SYNPO slope predicted DCMED (FIG. 6, p=0.02). SYNPO improved in 6/8 without DCMED and 1/5 with DCMED NSE and COX IV were not useful biomarkers in neuronal exosomes in this sample.

Improvement in levels of the neuronal survival protein SYPO in neural exosomes released into the neonatal circulation between 8 and 14 h of head cooling is a powerful indicator of favorable short term clinical outcomes and is superior to predictions based on cord blood pH or BE.

Example 4: Non-Invasive Assessment of Fetal CMV Infection and Injury Via Fetal Neuronal Exosomes: A Non-Human Primate Model Approximately 1 in every 150 neonates is born with congenital cytomegalovirus (CMV) infection, yet clinical outcomes range from unaffected to severe disability. Limited prenatal diagnostic tools constrain the accuracy of prognostic counseling, especially in the absence of significant sonographic pathology.

Rhesus macaque fetuses were inoculated intraperitoneally under ultrasound guidance with rhesus CMV (RhCMV) in the late 1st/early 2nd trimester. Fetal tissues were harvested in the late 3rd trimester. Maternal blood samples were collected at both time points. Fetal neuronal exosomes (FNEs) were isolated from maternal serum using previously published methods. RhCMV viral copy number was quantified in FNEs and fetal brain using standard PCR protocols. RE1-Silencing Transcription Factor (REST), neurogranin and synaptophysin were quantified using commercial ELISA kits and normalized to CD81. Pre-Post infection levels of exosomal proteins were compared (paired Student's t-test).

Ten mother-infant pairs were studied. One fetal demise was found at harvest. CMV could be detected in 6 of 10 fetal brains. No gross pathology or ultrasound changes were noted. When comparisons were restricted to cases with detectable brain CMV, infection did not alter FNE neurogranin or synaptophysin. However FNE REST decreased significantly following infection (1697.2±40.4 vs. 1369.0±58.9 pg/mL, p=0.02). There was a strong negative correlation between FNE neurogranin and parietal lobe CMV viral copy number that did not reach statistical significance (r=−0.826, p=0.085). FNE REST and neurogranin appeared positively correlated (r=0.772, p=0.07). FNE CMV viral copy number was low but not undetectable.

REST is an essential modulator of neuronal differentiation and plasticity and serves a critical role in repressing pro-apoptotic genes. In this non-human primate model of mild congenital disease, neural CMV infection was associated with decreased FNE REST. Larger studies are needed to explore the potential that FNE REST could be developed into a clinically useful, non-invasive, prenatal diagnostic tool. Non-infected comparators are required to control for unknown gestational age changes in REST.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for isolating a fetal exosome from a biological sample, the method comprising:
    obtaining a biological sample from a pregnant subject;
    isolating a total exosome population from the biological sample;
    contacting the total exosome population with a Contactin-2/TAG1 antibody conjugated to a label;
    contacting the antibody with a substrate comprising a moiety that binds the label to form a complex consisting of the substrate, the antibody and the fetal exosome; and
    isolating the complex.

2. The method of claim 1, wherein the fetal exosome is a fetal neural exosome.

3. The method of claim 1, wherein the biological sample is plasma.

4. The method of claim 1, wherein the label is biotin and the substrate comprises streptavidin.

5. The method of claim 1, wherein the subject is human.

* * * * *